US008115061B2

(12) United States Patent
Risacher et al.

(10) Patent No.: US 8,115,061 B2
(45) Date of Patent: Feb. 14, 2012

(54) PLANT TRANSFORMATION METHOD

(75) Inventors: Thierry Risacher, Cambridge (GB); Melanie Craze, Sandy (GB)

(73) Assignee: Biogemma S.A.S., Paris (FR)

( * ) Notice: Subject to any disclaimer, the term of this patent is extended or adjusted under 35 U.S.C. 154(b) by 0 days.

(21) Appl. No.: 12/891,056

(22) Filed: Sep. 27, 2010

(65) Prior Publication Data

US 2011/0078827 A1    Mar. 31, 2011

Related U.S. Application Data

(63) Continuation of application No. 11/837,143, filed on Aug. 10, 2007, now Pat. No. 7,803,988, which is a continuation of application No. 09/959,137, filed as application No. PCT/EP00/04177 on Apr. 19, 2000, now Pat. No. 7,285,705.

(30) Foreign Application Priority Data

Apr. 19, 1999 (EP) .................................... 99420097

(51) Int. Cl.
*C12N 15/84* (2006.01)
*A01H 4/00* (2006.01)
(52) U.S. Cl. ........ 800/294; 800/306; 800/307; 800/312; 800/317.1; 800/322; 435/430.1; 435/469
(58) Field of Classification Search ........................ None
See application file for complete search history.

(56) References Cited

U.S. PATENT DOCUMENTS

| | | | |
|---|---|---|---|
| 5,024,944 A * | 6/1991 | Collins et al. | 800/294 |
| 5,102,796 A | 4/1992 | Hall et al. | |
| 5,994,624 A | 11/1999 | Trolinder et al. | |
| 6,664,109 B2 * | 12/2003 | Shewmaker et al. | 435/469 |

FOREIGN PATENT DOCUMENTS

| | | |
|---|---|---|
| EP | 0672752 A1 | 9/1995 |
| EP | 0870838 | 10/1998 |
| WO | WO-8600931 | 2/1986 |
| WO | WO-9748814 | 12/1997 |
| WO | WO-9856932 | 12/1998 |
| WO | WO-9914349 | 3/1999 |

OTHER PUBLICATIONS

Moloney et al. Plant Cell Reports 8(4): 238-242 (Apr. 1989).*
Spaink et al., The Rhizobiaceace. eds. Spaink et al., p. xiii. 1998.
Clough et al., The Plant Journal, 1998, vol. 16, No. 6, pp. 735-743.
Raven et al., Biology of Plants, 1992, Worth Publishers, New York, NY 10003, p. 395, figure 18-3 and text.
Zambryski et al., The EMBO Journal, vol. 2, No. 12, pp. 2143-2150, 1983.
Graves et al., Journal of Bacteriology, vol. 169, No. 4, pp. 1745-1746, Apr. 1987.

* cited by examiner

*Primary Examiner* — David T Fox
(74) *Attorney, Agent, or Firm* — Connolly Bove Lodge & Hutz LLP

(57) ABSTRACT

The invention provides a transformation method comprising inoculation and co-cultivation of a target tissue, from a target plant, with *Agrobacterium*, at a time when the target tissue is in its natural plant environment, followed by generation of a transgenic plant via dedifferentiation and regeneration of the target tissue.

6 Claims, 8 Drawing Sheets

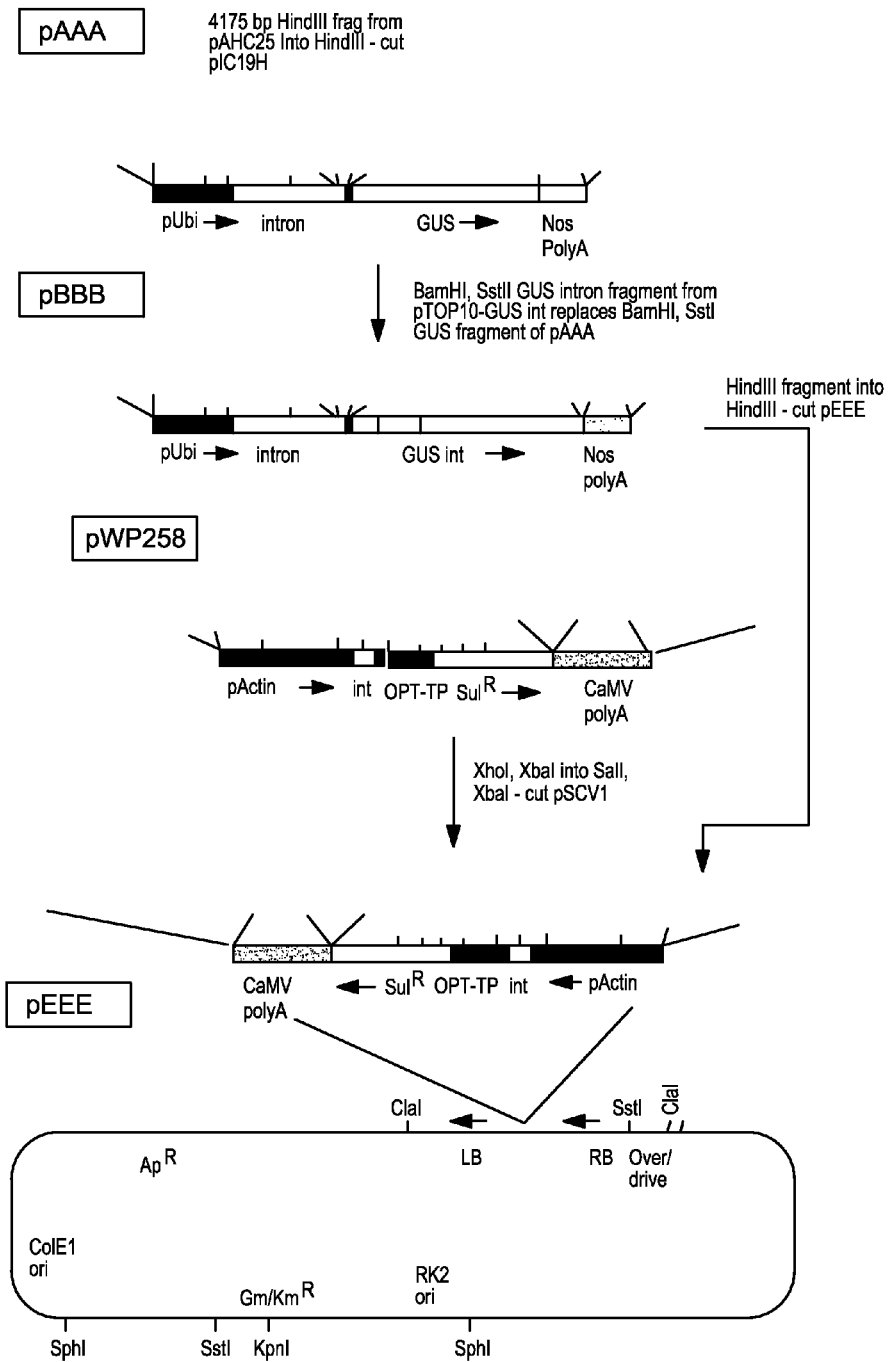
Figure 1: Cloning strategy for pSCV sulugI

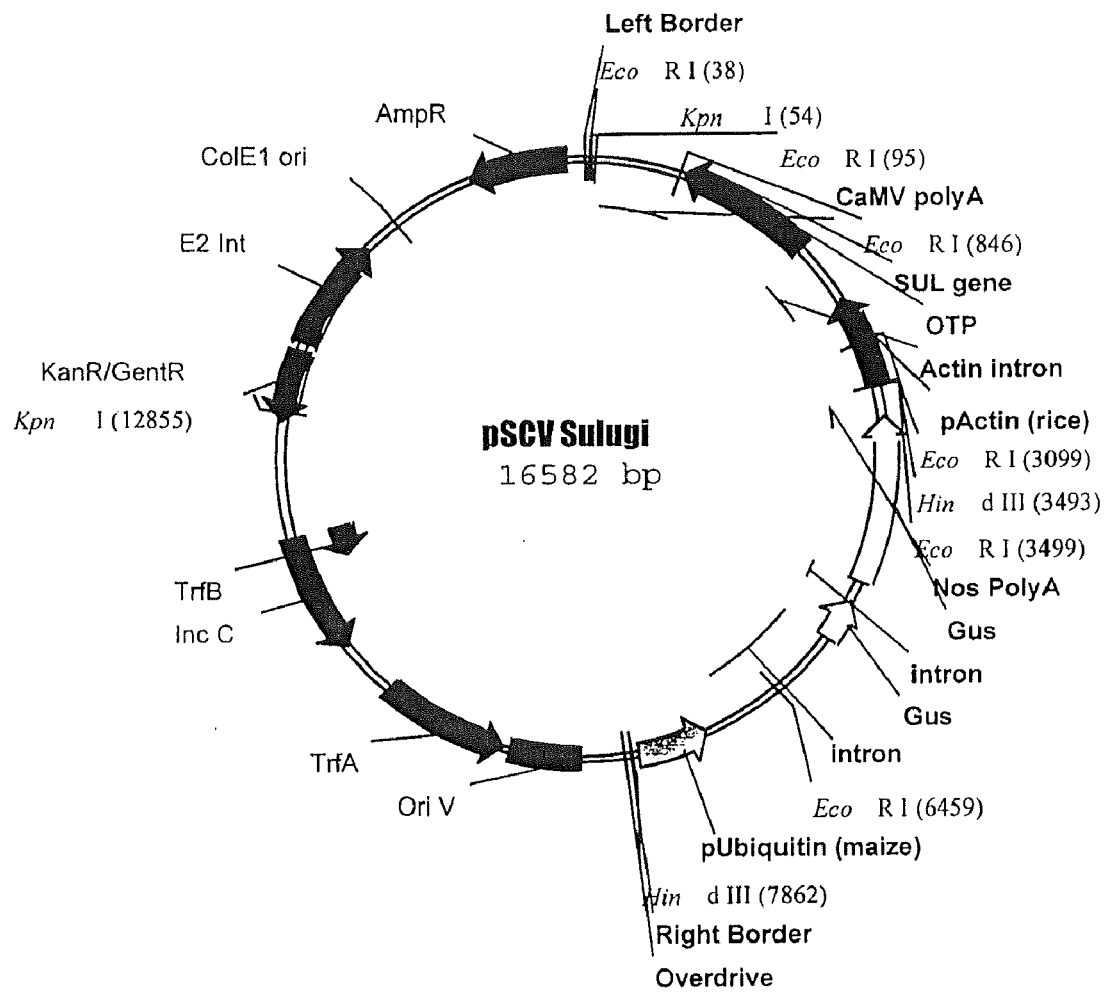
Figure 2 : pSCV Sulugi

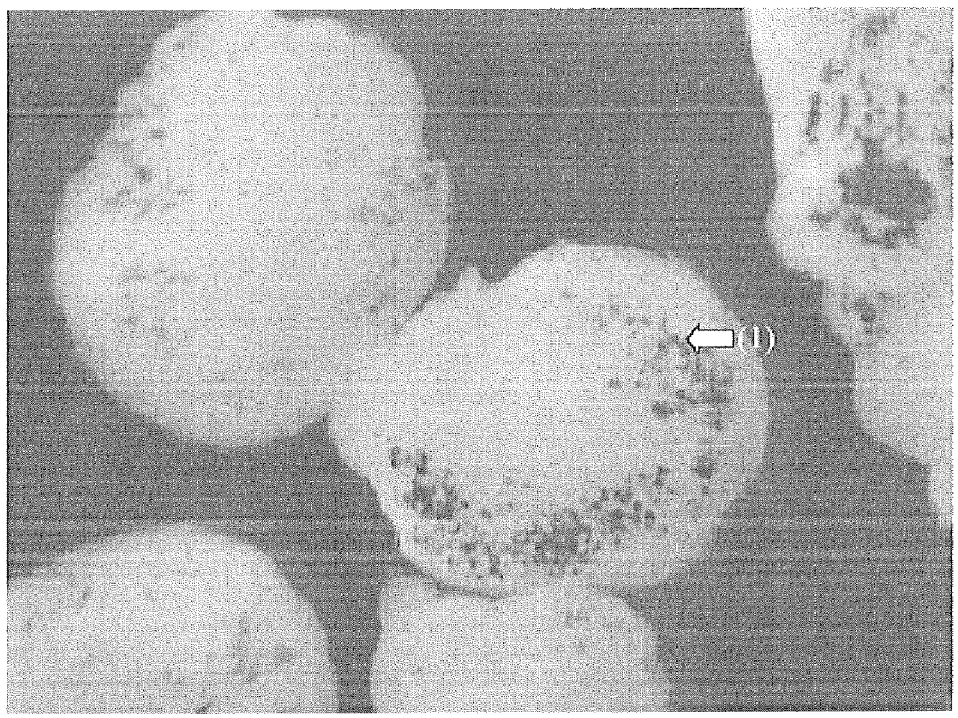
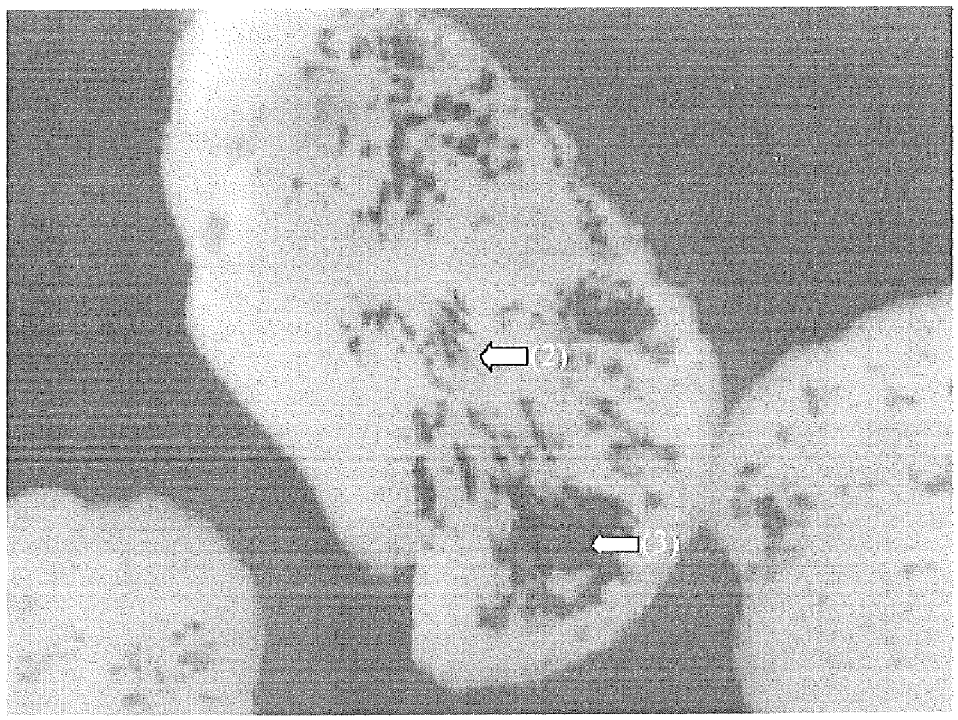
Figure 3 : Transient expression with wheat immature embryos
(1) Standard blue GUS spots
(2) Small blue dashes comprising several linked cells
(3) Large areas of blue staining

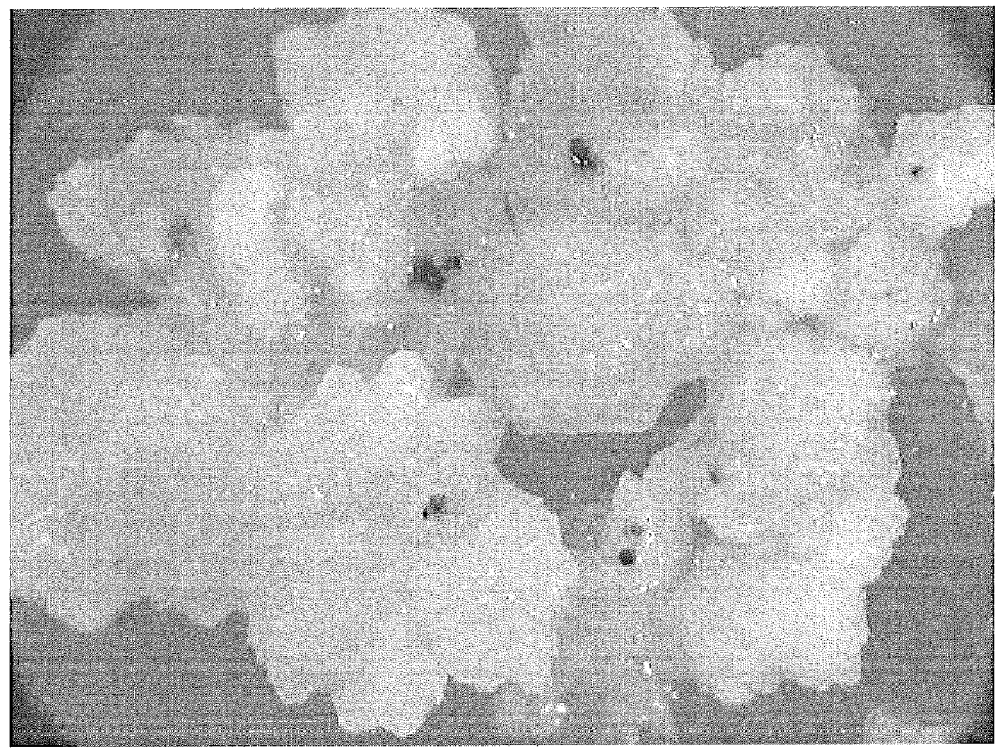
Figure 4: Stable GUS expression in wheat callus

Figure 5 : Stable GUS expression (detail) in wheat

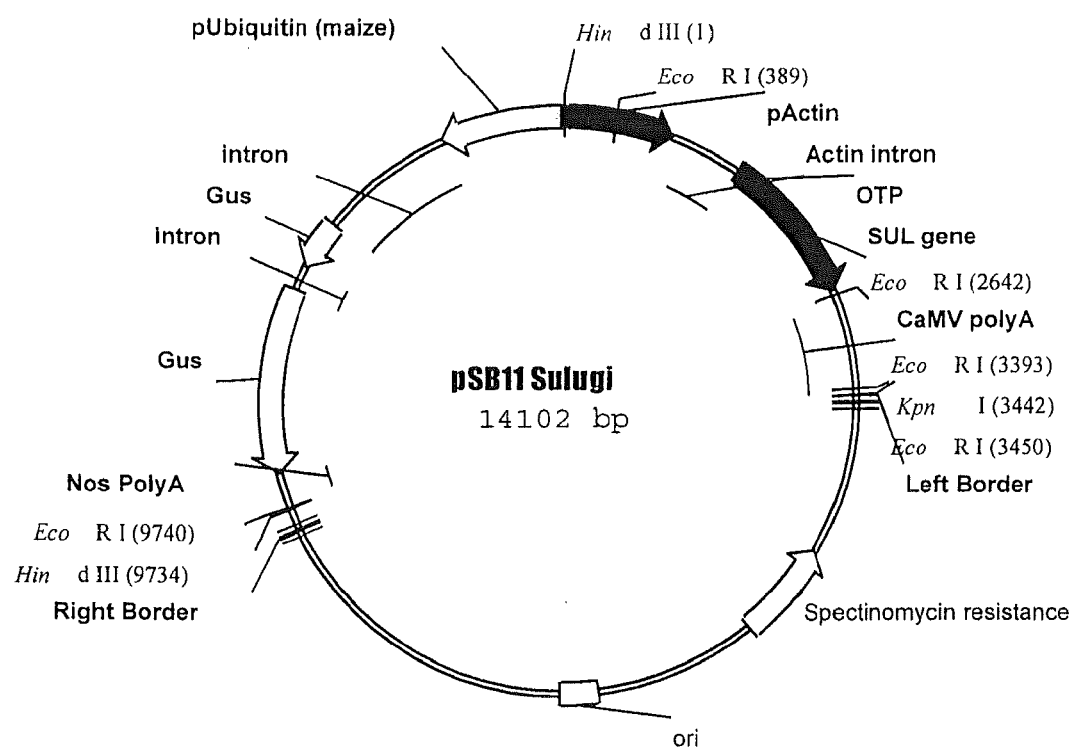
Figure 6: pSB11Sulugi

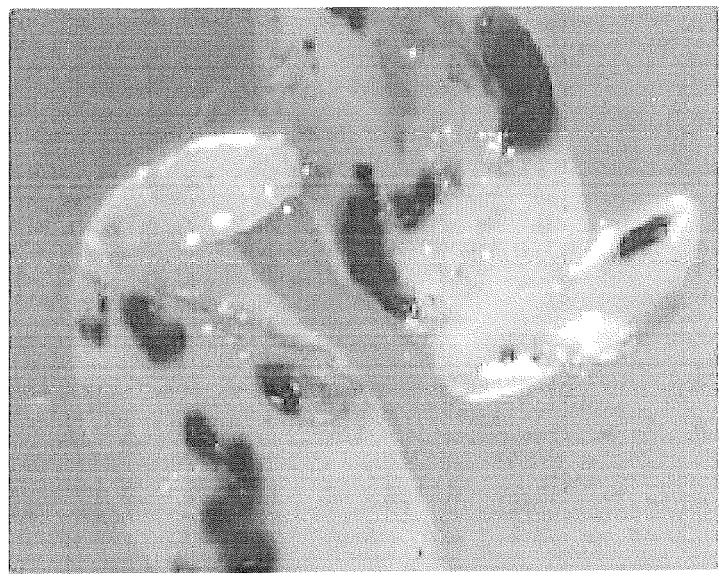
Figure 8: Example of transient GUS expression in soybean immature cotyledons

PLANT TRANSFORMATION METHOD

RELATED APPLICATIONS

This application is a continuation of application Ser. No. 11/837,143 filed on Aug. 10, 2007, now U.S. Pat. No. 7,803,988, which is a continuation of application Ser. No. 09/959,137 filed on Feb. 8, 2002, now U.S. Pat. No. 7,285,705, which is a national stage application (under 35 U.S.C. §371) of International Application PCT/EP00/04177 filed Apr. 19, 2000, which claims benefit of European Patent Office Application Serial No. EP 99420097.0 filed on Apr. 19, 1999.

BACKGROUND OF THE INVENTION

The present invention provides a method for the *Agrobacterium*-mediated transformation of plants, in particular monocotyledonous plants.

The invention is in the field of plant transformation, in particular cereal transformation, specifically in the use of *Agrobacterium tumefaciens* or any other *Agrobacterium* species (hereinafter referred to as *Agrobacterium*). Until recently, only direct transformation methods could be used to produce transgenic cereal plants. Bombardment using a particle gun is the most widely accepted method to this end. More recently, reports have appeared in the literature showing that some of the cereals can be genetically modified using *Agrobacterium* (Hiei et al, Plant Mol. Biol. (1997) 35:205-218); Ishida et al, Nature Biotechnol. (1996) 14:745-750; Cheng et al, Plant Physiol. (1997) 115:971-980; Tingay et al., The Plant Journal, 11:1369-1376 (1997)).

Transformation efficiencies reported in the literature show wide variability for different cereals. Typically, low figures have been quoted for maize (Ishida 1996), with a system that is highly genotype dependent. With rice, low efficiencies for transformation have also been reported, and particularly low levels have been shown for wheat. In all of these systems, *Agrobacterium* is applied in vitro, to isolated tissue that is either in the process of de-differentiation or is already de-differentiated.

As described above, systems for *Agrobacterium*-mediated transformation of cereals have been reported in rice (Hiei, 1997), maize (Ishida, 1996), wheat (Cheng, 1997) and barley (Tingay, 1997). A common feature of these methods is that explants, preferably immature embryos or embryogenic calli derived therefrom, are isolated from a donor plant and inoculated with *Agrobacterium* in vitro.

Hess and coworkers (Plant Science 72: 233-244, 1990) attempted transformation of wheat by pipetting *Agrobacterium* into spikelets of wheat. The authors objective in this report was to achieve gene transfer by transformation of pollen and to subsequently recover transformed seed following normal fertilization. Removal of tissue from the inoculated spikelet for subsequent selection and regeneration in culture was not attempted or suggested.

Other workers have reported the *Agrobacterium*-mediated transformation of maize and rice by inoculation of shoot apices (Gould J (1991) Plant Physiol. 95: 426-434; Park S H (1996) Plant Molecular Biology 32: 1135-1158). Once again, this was with the object of transforming the germ line and thus recovering transformed seed. This pathway of regeneration is distinct from that employed in the method of our invention: in fact, a specified aim of these methods is to avoid any method of plant regeneration going through dedifferentiation of tissue and adventitious regeneration.

U.S. Pat. Nos. 5,177,010 and 5,187,073 (Goldman, et al) disclose a method for transforming corn and Gramineae respectively, comprising wounding newly emerged seedlings and inoculating with *Agrobacterium*. Once again, the objective of this method is to transform germ line cells in the seedling that will subsequently give rise to reproductive organs in the mature plant and thereby recover transformed pollen from the plant.

Another process that has been studied by those trying to develop cereal transformation is agroinfection. U.S. Pat. No. 5,569,597 (Grimsley, et al) discloses a method of introducing viral DNA into plants using *Agrobacterium*. Following inoculation of maize seedlings with *Agrobacterium* having DNA from maize streak virus inserted in its T-DNA, the inventors observed the appearance of disease symptoms, indicating proliferation of virus in plant cells. The *Agrobacterium* therefore acts as a vehicle to introduce the viral DNA into the plant, after which the virus is able to cause a systemic infection. However, there is no evidence that agroinfection results in plant transformation i.e. transfer of viral DNA to the plant genome. In so far as the patent considers transformation it is, once again, with a view to targeting meristematic tissues in order to achieve transformation of germ cells.

SUMMARY OF THE INVENTION

In this novel method, the targeted tissue is inoculated and co-cultivated with *Agrobacterium* when the target tissue is within its natural plant environment. In this way, the target tissue is still developing along normal physiological and temporal pathways. The target tissue is then removed from its normal environment and directed along a pathway of dedifferentiation and regeneration to form a transgenic plant. Advantageously, the transgenic plant is a fertile transgenic plant.

DETAILED DESCRIPTION OF THE INVENTION

In the present invention, the term <<within its natural plant environment>> includes all conditions where the target tissue is able to develop along substantially normal physiological and temporal pathways. Such conditions include the target tissues being in vivo, the target tissue still being within, on or attached to the plant (for example the target tissue being an embryo within a seed on a cut tiller), or target tissue which is still in the same cellular environment that it would be if it were still on the plant (for example the target tissue being an embryo within an isolated seed, or part of an isolated seed). Other examples include immature inflorescence still within the leaf sheath or at least still attached to the plant and an immature anther while still in the unopened flower bud.

Dedifferentiation means cell clusters, such as callus, that show unorganized growth.

In addition to the target tissue being in an environment equal to that on the plant, the *Agrobacterium* is in an environment that is more analogous to the bacteria's natural environment. Accordingly the *Agrobacterium* is likely to act more efficiently in its transformation of the target tissue than when it is directed to an isolated tissue in a petri dish, as in the art.

One consequence of these two factors is the opportunity to obtain a higher transformation efficiency of the desired transgene to the target tissues and thus a higher transformation efficiency for the production of transgenic plants.

One of the primary steps involved in most transformation protocols involves wounding the target tissue. With *Agrobacterium*, this can be for two reasons—to expose the cells thought to be responsive to transformation and that are capable of regeneration, (particularly for Gramineous species) and to induce the *Agrobacterium* to transfer its T-DNA.

One published method for wheat that does not involve wounding still involves the use of a wetting agent (Silwet or pluronic acid) or vacuum infiltration (WO 97/48814). All these processes involve some inherent damage to the tissue, and an associated reduction in regenerative capability.

In a preferred embodiment of the present invention, wounding of the target cells in the target tissue is kept to a minimum or totally excluded—although a wetter may be used, it is not essential. Some gross damage of tissue may occur during the delivery procedure, but even then the vast majority of regenerable cells that are subsequently targeted by the *Agrobacterium* remain undamaged and their regenerative capacity is unaffected.

According to the present invention, inoculation of *Agrobacterium* is preferably done by the application of an *Agrobacterium* suspension to the target tissue by an appropriate delivery device, such as a syringe, for example a Hamilton syringe.

According to the present invention, there is developed a system for the *Agrobacterium* mediated transformation of plants, preferably cereals, involving infection of target tissue. The system has been shown to be highly efficient, and very reproducible.

The target tissue may be any tissue which can subsequently be placed in a tissue culture phase and a plant regenerated. Particularly suitable target tissue, according to the present invention include an embryo, an inflorescence, an ovary, a leaf base, or an anther. The embryo, inflorescence, ovary or anther are preferably immature.

In another preferred embodiment of the invention, when the target tissue is an embryo, the target area for inoculation is the interface between two layers of cells that are in tight contact, i.e. the developing scutellum surface and adjoining starch parenchyma of endosperm. *Agrobacterium* has to be delivered to this interface with minimum damage to the target tissue to the extent that its regenerative capacity is not adversely affected. It could not be predicted from what is known in the field that such an effective, and reproducible, technique could be generated.

In the transformation method of the invention, the target tissue is inoculated and co-cultivated with *Agrobacterium*. Following this, a transgenic plant is regenerated by dedifferentiation and regeneration of the target tissue. Thus, following the inoculation and co-cultivation, the target tissue is made to dedifferentiate. From this dedifferentiated tissue a plant is obtained by standard procedures known in the art. Following inoculation and co-cultivation, the target tissue is preferably transferred into a more suitable environment for the required dedifferentiation and subsequent regeneration of a plant. Thus, at least part of the dedifferentiation of the target tissue (following inoculation and cultivation) is carried out in vitro. Regeneration of the plant is also preferably carried out in vitro.

One surprising feature of the method according to the present invention (at least for wheat immature embryos) is the frequent production of multiple transformation events from one isolated explant. In the art (Cheng et al, 1997) all plants derived from the same explant are usually considered to be clones of a given event. With this method, this assumption cannot be made as one explant frequently gives rise to several plants, each with a distinct integration pattern when analyzed by Southern blot. One possible explanation of this, which should not be interpreted as limiting to the invention, could be the absence of wounding of the most regenerable cells before the *Agrobacterium* is applied. More of the T-DNA transfers are likely to take place in cells that still have the capability to develop further.

One feature of cereal transformation, often described as crucial, is the induction of *Agrobacterium* with the inclusion, in the inoculation and/or co-cultivation media, of an *Agrobacterium* vir inducing agent (Hiei et al., 1997, Cheng et al., 1997). Such inducing agents include acetosyringone, vanillin, ferulic acid, catechol, and syringic acid. The present invention demonstrates successful *Agrobacterium* transformation in cereals where no inducing agent was necessary. In particular, successful *Agrobacterium* transformation of wheat was obtained with no inducing agent, showing that no inducing agent was necessary for efficient T-DNA delivery. Where the target tissue of the present invention is an immature embryo and its natural plant environment is provided by an immature seed, it is postulated that the *Agrobacterium* appears to be sufficiently induced naturally, by cells of the immature embryo. One possible explanation of this, which should not be interpreted as limiting to the invention could be that it is the cells which form the <<natural plant environment>> adjacent or around the target tissue which are responsible for the *Agrobacterium* induction. Removal of the embryo from its natural plant environment appears to deprive the target tissue of available substances which may assist in the *Agrobacterium* induction.

The present invention enables the introduction of a desired transgene or heterologous nucleic acid into plant tissue and the ability to obtain a fertile transgenic plant. It is particularly useful for the production of transgenic monocotyledonous plants since known transformation methods are associated with difficulties and low efficiencies of transformation. Suitable monocotyledonous plants include asparagus, onion, oil palm, yam, banana, in particular any species from the Gramineae family, especially cereals (those grasses whose fruit are used for human food) such as wheat, barley, maize, rice, oats, rye, sorghum and millet.

This method is also applicable to dicotyledonous species, particularly where a tissue culture system exists, or may be developed, that includes a callus phase. Suitable dicotyledonous plants include rape, pea, pepper, soybean, sunflower, sugar beet and cucurbit and trees, such as rubber, pines and eucalyptus.

In accordance with the present invention, the heterologous nucleic acid is one which is not normally found in *Agrobacterium* T-DNA or the plant that is to be transformed. As used herein, the term heterologous nucleic acid includes all synthetically engineered and biologically derived genes which may be introduced into a plant by genetic engineering, including but not limited to non-plant genes, modified genes, synthetic genes, portion of genes, and genes from any plant species. The heterologous nucleic acid preferably contains the coding region of a protein or polypeptide or antisense molecule of interest, with flanking regulatory sequences that promote the expression thereof in the resulting monocot.

Methods for constructing heterologous nucleic acids for successful transformations of plants are well known to those skilled in the art, and the same methods of construction may be utilized to produce the heterologous nucleic acids useful herein. Weising et al. (1988) (Annual Rev. Genet. 22:241), the subject matter of which is incorporated herein by reference, describe suitable components which include promoters, polyadenylation sequences, selectable marker genes, reporter genes, enhancers, introns, and the like, and provide suitable references for compositions thereof. Sambrook et al. (1989) (Molecular Cloning: A Laboratory Manual, Cold Spring Harbor, N.Y.), provide suitable methods of construction.

Generally the plasmid comprising the nucleic acid heterologous gene will be relatively small, i.e. less than about 30 kb, to minimize any susceptibility to physical, chemical, or enzymatic degradation which is known to increase as the size of the gene increases.

Suitable transgene or heterologous nucleic acids for use herein include all nucleic acids that will provide or enhance a beneficial feature of the resultant transgenic plant. For example, the nucleic acid may encode proteins or antisense RNA transcripts in order to promote increased food values, higher yields, pest resistance, disease resistance, and the like. Representative nucleic acids include, for example, a bacterial dap A gene for increased lysine; Bt-endotoxin gene or protease inhibitor for insect resistance; lytic peptides genes for disease resistance, bacterial or plant EPSPS for resistance to glyphosate herbicide (U.S. Pat. No. 4,940,835, U.S. Pat. No. 5,188,642, U.S. Pat. No. 4,971,908, U.S. Pat. No. 5,145,783, U.S. Pat. No. 5,312,910, U.S. Pat. No. 5,633,435, U.S. Pat. No. 5,627,061, U.S. Pat. No. 5,310,667, WO 97/04103); bacterial or plant HPPD (WO 96/38567, WO 98/02562) for resistance to HPPD-inhibitor herbicides (i.e. diketones, isoxazoles, etc.), bar or pat genes for resistance to glufosinate, chitinase or glucan endo 1,3-B-glucosidase for fungicidal properties. Also, the nucleic acid may be introduced to act as a genetic tool to generate mutants and/or assist in the identification, genetic tagging, or isolation of segments of plant genes.

Examples of genes useful for modifying quality include: genes for starch biosynthetic or degrading enzymes e.g. starch synthases, starch branching enzymes (for example SBEI, SBEII, SSSI and DBEI from wheat disclosed in WO99/14314), and grain storage protein genes e.g. sub-unit proteins of glutenin (for example see WO97/25419), gliadins, hordeins. Artificial male sterility genes e.g. barnase (EP-A-0344029), and PR-glucanase (WO92/11379) under the control of a suitable promoter are also useful for the production of hybrid seed.

Genes may also be introduced for the purpose of producing pharmaceutically active compounds in plant or for improving the nutritional quality of plants (biopharming and functional foods).

Additional examples may be found in Weising, supra.

The plasmid comprising the heterologous nucleic acid to be introduced into the plant further will generally contain either a selectable marker or a reporter gene or both to facilitate identification and selection of transformed cells. Alternatively, the selectable marker may be carried on a separate vector and used in a cotransformation procedure. Both selectable markers and reporter genes may be flanked with appropriate regulatory sequences to enable expression in plants. Useful selectable markers are well known in the art and include, for example, antibiotic and herbicide resistance genes. Specific examples of such genes are disclosed in Weising et al, supra. A preferred selectable marker gene is the sul gene conferring resistance to sulfonamides (EP-B-0369637). Other selectable markers known in the art include the hygromycin B phosphotransferase (hpt) coding sequence which may be derived from E. coli, the aminoglycoside phosphotransferase gene of transposon Tn5 (AphII) which encodes resistance to the antibiotics kanamycin, neomycin, and G418, as well as those genes which code for resistance or tolerance to glyphosate, bialaphos, methotrexate, imidazolinones, sulfonylureas, bromoxynil, dalapon, and the like. Selectable marker genes that confer herbicide tolerance are also of commercial utility in the resulting transformed plants.

Reporter genes which encode easily assayable marker proteins are well known in the art. In general, a reporter gene is a gene which is not present or expressed by the recipient organism or tissue and which encodes a protein whose expression is manifested by some easily detectable property, e.g. phenotypic change or enzymatic activity. Examples of such genes are provided in Weising et al, supra. Preferred genes include the chloramphenicol acetyl transferase (cat) gene from Tn9 of E. coli, the beta-gluronidase (gus) gene of the uidA locus of E. coli, the green fluorescence protein (GFP) gene from Aequoria victoria, and the luciferase (luc) gene from the firefly Photinus pyralis.

The regulatory sequences useful herein include any constitutive, inducible, tissue or organ specific, or developmental stage specific promoter which can be expressed in the particular plant cell. Suitable such promoters are disclosed in Weising et al, supra. The following is a partial representative list of promoters suitable for use herein: regulatory sequences from the T-DNA of A. tumefaciens, including mannopine synthase, nopaline synthase, and octopine synthase; alcohol dehydrogenase promoter from corn; light inducible promoters such as ribulose-biphosphate-carboxylase small subunit gene from a variety of species and the major chlorophyll a/b binding protein gene promoter; histone promoters (EP 507 698), actin promoters; maize ubiquitin 1 promoter (Christensen et al. (1996) Transgenic Res. 5:213); 35S and 19S promoters of cauliflower mosaic virus; developmentally regulated promoters such as the waxy, zein, or bronze promoters from maize; as well as synthetic or other natural promoters which are either inducible or constitutive, including those promoters exhibiting organ specific expression or expression at specific development stage(s) of the plant, like the alpha-tubulin promoter disclosed in U.S. Pat. No. 5,635,618.

Other elements such as introns, enhancers, polyadenylation sequences and the like, may also be present in the nucleic acid. These elements must be compatible with the remainder of the gene constructions. Such elements may or may not be necessary for the function of the gene, although they may provide a better expression or functioning of the gene by effecting transcription, stability of the mRNA, or the like. Such elements may be included in the nucleic acid as desired to obtain the optimal performance of the transforming gene in the plant. For example, the maize AdhlS first intron maybe placed between the promoter and the coding sequence of a particular heterologous nucleic acid. This intron, when included in a gene construction, is known to generally increase expression in maize cells of a protein. (Callis et al. (1987) Genes Dev. 1:1183). Other suitable introns include the first intron of the shrunken-1 gene of maize (Maas et al. (1991) Plant Mol. Biol. 16:199); the first intron of the castor bean catalase (cat-1) gene (Ohta et al, (1990) Plant Cell Physiol. 31:805); potato catalase second intron of the ST-LSI gene (Vancanneyt et al. (1990) Mol. Gen. Genet. 220:245); tobacco yellow dwarf virus DSV intron (Morris et al. (1992) Virology 187:633; actin-1 (act-1) intron from rice (McElroy et al. (1990) Plant Cell 2:163); and triose phosphate isomerase (TPI) intron 1 (Snowden et al. (1996) Plant Mol. Biol. 31:689). However, sufficient expression for a selectable marker to perform satisfactorily can often by obtained without an intron. (Battraw et al. (1990) Plant Mol. Biol. 15:527).

The plasmid comprising the heterologous nucleic acid may also comprise sequences coding for a transit peptide, to drive the protein coded by the heterologous gene into the chloroplasts of the plant cells. Such transit peptides are well known to those of ordinary skill in the art, and may include single transit peptides, as well as multiple transit peptides obtained by the combination of sequences coding for at least two transit peptides. One preferred transit peptide is the Optimized Transit Peptide disclosed in U.S. Pat. No. 5,635,618, comprising in the direction of transcription a first DNA sequence encoding a first chloroplast transit peptide, a second DNA sequence encoding an N-terminal domain of a mature protein naturally driven into the chloroplasts, and a third DNA sequence encoding a second chloroplast transit peptide.

To determine whether a particular combination of heterologous nucleic acid and recipient plant cells are suitable for use herein, the plasmid may include a reporter gene. An assay for expression of the reporter gene may then be performed at a suitable time after the heterologous nucleic acid has been introduced into the recipient cells. A preferred such assay entails the use of the *E. coli* beta-glucuronidase (gus) gene described by Jefferson et al. (1987) EMBO J. 6:3901, incorporated herein by reference.

A use of the present invention is the production of a fertile transgenic plant, which comprises one or more transgenes of interest. The seeds, or other propagating material from such a plant may be used to prepare subsequent generations of transgenic plants (including offspring) which comprise the one or more transgenes from the original method. Such subsequent generations of plants (including offspring), and propagating material, including seeds are also included in the scope of the present invention.

A second aspect of the invention provides the use of *Agrobacterium* in a transformation method comprising inoculation and co-cultivation of a target tissue with *Agrobacterium*, at a time when the target tissue is in its natural plant environment, followed by generation of dedifferentiated tissue from the target tissue.

The dedifferentiated tissue may optionally be regenerated into a transgenic plant. However, the second aspect of the invention is also advantageous in situations where the dedifferentiated tissue (itself, or any non-whole plant generated from it) is of use. Such situations include: storing of the dedifferentiated tissue for periods before further use; and recovery of useful plant products, such as secondary plant metabolites, for example, from cell culture. All preferred features of the first aspect of the invention, as described above, also apply to the second.

According to the first and second aspects of the invention, the transformed dedifferentiated tissue obtained may be regenerated. It may be regenerated to form, for example, callus tissue, whole plants, fertile whole plants, roots, shoots, seeds or other propagating material.

A third aspect of the invention provides the use of *Agrobacterium* in a transformation method comprising inoculation and co-cultivation of a target tissue with *Agrobacterium*, at a time when the target tissue is in its natural plant environment, followed by generation of transgenic plant material via dedifferentiation and optionally regeneration of the target tissue.

The transgenic plant material obtained according to the third aspect of the invention may be callus, a whole plant (preferably fertile), roots or shoots, seeds or other propagating material.

All preferred features of aspects 1 and 2 also apply to the third aspect.

A fourth aspect of the invention provides transformed plant tissue obtained by a method according to the first or second aspects of the invention. Such transformed plant tissue includes callus, root material, shoot material, whole plants, seeds or other propagating material. The plants are most preferably fertile plants.

There are various reasons why the present invention is successful and why the target tissue is more susceptible to transformation by *Agrobacterium* while still in a natural plant environment. While not intending to limit the invention in any way, the following are proposed reasons as to why the present invention is successful:

1. The target cells, in their natural plant environment are rapidly dividing, probably more so than in tissue culture.
2. Avoiding a post-isolation treatment (i.e. inoculation and co-cultivation) increases the potential for callus formation and also regeneration potential
3. Different cells of the developing target tissue are exposed to *Agrobacterium* (compared to the art), specifically those that may be sub-epidermal and thought to be more regenerable
4. The absence of wounding (a pre-requisite for most other cereal transformation protocols) renders almost all cells that have been transformed capable of subsequent development.
5. Amalgamating the two steps of inoculation and co-cultivation reduces the stresses usually placed on the target tissue by these two separate tissue culture steps.
6. The natural environment of the seed is more propitious for normal cell development, in the presence of the *Agrobacterium*, than removal to a tissue culture environment.
7. Surface cells will be softer in any target tissue and provide less of a barrier to the *Agrobacterium* than once exposed to air.

The transformation method of the present invention can be described according to the following <<general>> methodology. A more detailed method is set out in the examples.

The following general methodology is described as applied to embryo inoculation (in the seed). The person skilled in the art will appreciate that the general method may be adapted to other target tissues.

Construct Preparation and Transfer to *Agrobacterium*

Binary, superbinary, pGreen or co-integrate vectors containing appropriate genes and selectable markers and/or reporter genes are transferred into *Agrobacterium* by one of various available methods e.g. triparental matings, electroporation. The *Agrobacterium* used can be any standard, usually disarmed, *Agrobacterium tumefaciens* or rhizogenes strain including, but not limited to, LBA4404 (Hoekma et al, Nature (1983) 303:179-180)
EHA101 (Hood et al, J Bacteriol. (1986) 168:1291-1301
Disarmed C58, for example pMP90 (Koncz and Schell, M. G. G. (1986) 204, 383-396
LBA4404 containing pTOK233 (Hiei et al, Plant J (1994) 6:271-282)

Preparation of *Agrobacterium* for Experiments

*Agrobacterium* is incubated in or on media with appropriate selective antibiotics at 25-30° C. for 2 or 3 days. Bacteria is then collected and re-suspended in TSIM1 (MS media with 100 mg/l myo-inositol, 10 g/l glucose, 50 mg/l MES buffer pH5.5) or another similar culture media, that may also containing acetosyringone. A wetter, e.g. pluronic acid F68 may also be included and other inducing agents for the *Agrobacterium* can optionally be used e.g. opines or other secondary plant metabolites.

Preparation of Plant Material

The starting material for this protocol is the inflorescence of a monocotyledonous (usually gramineous) plant, some time after anthesis has occurred. All stages of the inoculation and co-cultivation can be carried out on the inflorescence while it is still on the intact plant. However, for ease and containment purposes, removal of the parts of the plant that carry the inflorescence is preferred. Nevertheless, the inflorescence remains in its natural plant environment even when the plant part carrying it is removed from the plant.

For example, wheat tillers, or those from any other cereal, approximately 8-16 days post-anthesis are harvested from glasshouse or Conviron (controlled environment room) grown plants. Immature seed are then exposed, but left attached to the plant, by whatever means necessary. For example, in wheat, the glumes of each spikelet and the lemma from the first two florets are carefully removed to expose the immature seed. Only these two seed in each spikelet are generally uncovered. This procedure is carried out along the entire length of the inflorescence.

Inoculation of Immature Seed

Agrobacterium suspension is inoculated into the immature seed approximately at the position of the scutellum: endosperm interface, using any appropriate delivery device for example, a Hamilton syringe. The volume of bacteria suspension delivered is usually 1 µl, but can vary depending on, for example, the seed size.

Tillers, for example, are then placed in water, or a nutritive solution, (optionally covered with a plastic bag to prevent seed dehydration) and placed in a lit incubator for 2-5 days (preferably 2 or 3 days). The temperature of the incubator can vary depending on the cereal species but will usually be in the range of 20-25° C.

Embryo Isolation and Culture

Following inoculation, immature seed are removed and surface sterilized. Immature embryos are isolated and placed on suitable callusing medium as exemplified by Weeks et al, Plant Physiol., 102:1077-1084, 1993; Vasil et al., Biotech. 11: 1553-1558, 1993; Ishida et al., 1996. Embryos are then successively transferred through any appropriate tissue culture procedure, including a selection step if required, that results in the regeneration of a transgenic plant, preferably a transgenic plant The present invention will now be described with reference to the following, non-limiting examples.

BRIEF DESCRIPTION OF THE DRAWINGS

FIG. 1, which shows a cloning strategy for pSCVsulugi

FIG. 2, which shows a plasmid map of pSCVsulugi.

FIG. 3, which shows transient GUS expression in an immature embryo, histochemically stained 4 days after in vivo inoculation and co-cultivation, showing blue spots and <<dashes>>.

FIG. 4, which shows areas of GUS expressing callus, histochemically stained one month after in vivo inoculation and co-cultivation, showing large dark blue stained areas.

FIG. 5, which shows detail of FIG. 4: showing a dark blue-stained and highly delineated area of callus with potential for regeneration.

FIG. 6, which shows a plasmid map of pSB11Sulugi

FIG. 8, which shows transient GUS expression in soybean immature cotyledons.

EXAMPLE 1

Figure 7:
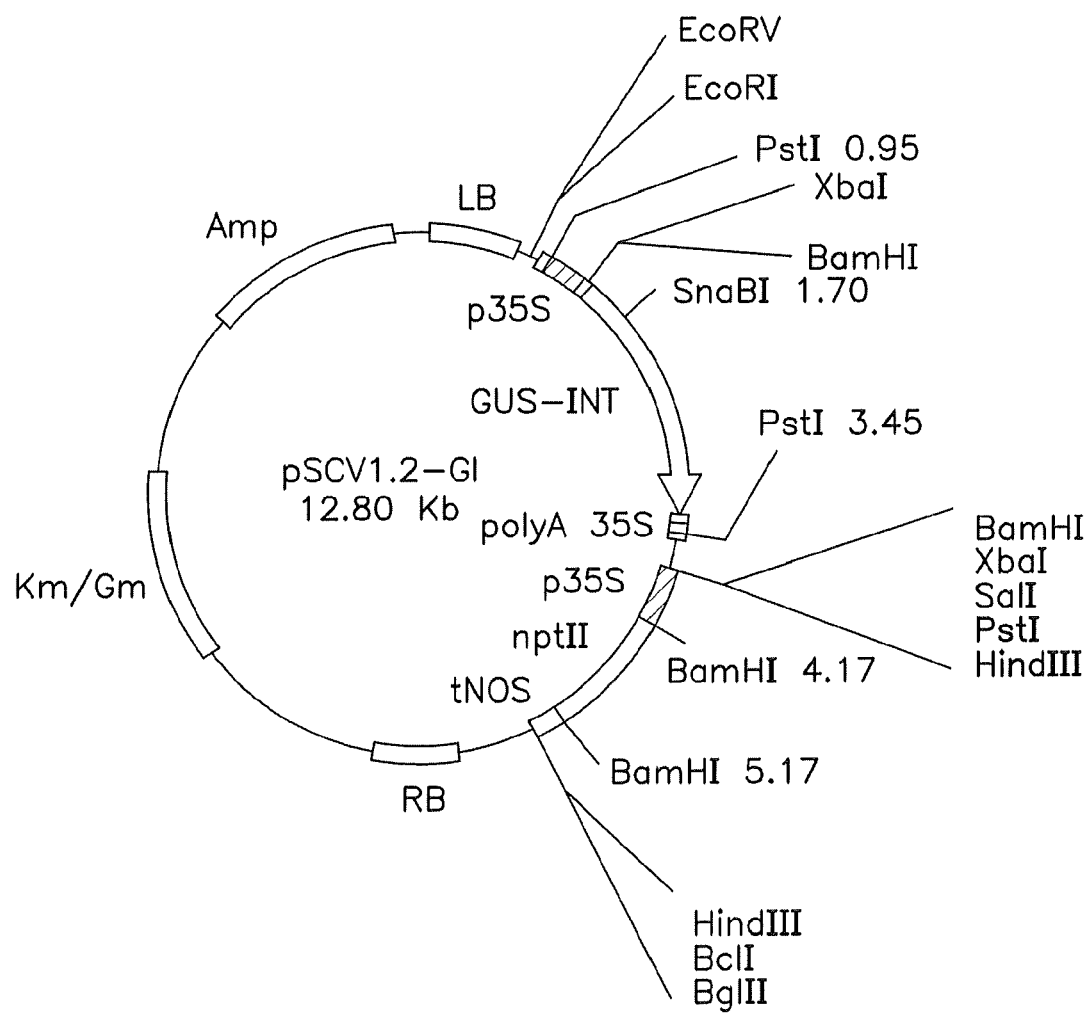
FIG. 7, which shows a plasmid map of pSCV1.2GI.

Transformation of Wheat by Seed Inoculation Method—Transient Expression and Production of Transformed Callus Construct Preparation For transformation purpose, the following constructs have been made (FIG. 1): The 4175 bp HindIII fragment from pAHC25 (Christensen et al, Plant Mol. Biol. (1992) 18:675-689) was introduced in pIC19H (Marsh et al, Gene (1984) 32:481-485) cut with HindIII (resulting plasmid pAAA). The BamHI, SstI GUS-intron fragment from pUC-Top10-GUS INT (Weinmann et al, Plant J. (1994) 5:559-569) replaces the BamHI, SstI GUS fragment from pAAA to give pBBB. The XhoI, XbaI fragment containing the Sul$^R$ from pWP258 (described in patent application WO98/49316) is introduced in SalI, XbaI cut pSCV1 (Firek et al, Plant Mol. Biol. (1993) 22:129-142) creating pEEE. The HindIII pUbi-GUSint fragment from pBBB is cloned into pEEE cut by HindIII, to form pSCVSulugi (see FIG. 2).

This construct was introduced into the disarmed supervirulent Agrobacterium tumefaciens strain EHA101, containing pEHA101 (Hood et al, J Bacteriol. (1986) 168:1291-1301) by electroporation and subsequent selection on 50 mg/l kanamycin and 70 mg/l gentamycin.

Preparation of Agrobacterium for Experiments

Agrobacterium was incubated on solidified YEP media with 20 mg/l kanamycin sulphate at 27° C. for 2 days. Bacteria was then collected and re-suspended in TSIM1 (MS media with 100 mg/l myo-inositol, 10 g/l glucose, 50 mg/l MES buffer pH5.5) containing 400 µM acetosyringone to an optical density of 2.4 at 650 nm.

Preparation of Plant Material

Wheat tillers of NB1 (a Spring wheat variety obtained from Nickerson Seeds Ltd, Rothwell, Lincs.), approximately 14 days post-anthesis (embryos approximately 1 mm in length) were harvested from glasshouse grown plants to include 50 cm tiller stem, (22/15° C. day/night temperature, with supplemented light to give a 16 hour day). All leaves were then removed except the flag leaf and the flag leaf cleaned to remove contaminating fungal spores. The glumes of each spikelet and the lemma from the first two florets were then carefully removed to expose the immature seed. Only these two seed in each spikelet were generally uncovered. This procedure was carried out along the entire length of the inflorescence. The ears were then sprayed with 70% IMS as a brief surface sterilization.

Inoculation of Tillers

Agrobacterium suspension (1 µl) was inoculated into the immature seed approximately at the position of the scutellum: endosperm interface, using a 10 µl Hamilton syringe, so that all exposed seed were inoculated. Tillers were then placed in water, covered with a translucent plastic bag to prevent seed dehydration, and placed in a lit incubator for 3 days at 23° C., 16 hr day, 45 µEm$^{-2}$s$^{-1}$ PAR.

Embryo Isolation and Culture

After 3 days of co-cultivation, inoculated immature seed were removed and surface sterilized (30 seconds in 70% ethanol, then 20 minutes in 20% Domestos, followed by thorough washing in sterile distilled water). Immature embryos (136 in total) were aseptically isolated and placed on W3 media (as described in patent application WO98/49316) with the addition of 150 mg/l Timentin (W3T) and with the scutellum uppermost (20 embryos per plate). Cultures were placed at 25° C. in the light (16 hour day, 80 µEm$^{-2}$s$^{-1}$ PAR).

After 3 days culture on W3T, 50 embryos were removed and put in X-gluc solution (Jefferson, Plant Mol. Biol. Rep. (1987) 5:386-405) at 37° C. for 16 hours, to assess GUS expression. The development of the embryonic axis on the remaining embryos was assessed 5 days after isolation and the axis was removed where necessary to improve callus production. Eight days post isolation a further 31 embryos were removed and stained as before.

The remaining 55 embryos were maintained on W3T for 4 weeks, with a transfer to fresh media at 2 weeks post-isolation.

One month after embryos were isolated, remaining embryo-derived callus was assessed for embryogenic capacity and stained for GUS expression.

Results

Histochemical Staining 4 Days Post-Inoculation

Some isolated embryos showed evidence of needle damage as a result of the inoculation procedure. This was very rarely associated with any of the GUS expression determined histochemically.

GUS expression in these embryos appeared in three forms
1. Standard blue GUS spots as documented in the art, see FIG. 3
2. Small dashes of blue comprising several linked cells all apparently expressing GUS to the same extent, see FIG. 3
3. Large blocks of dark blue staining on the scutellum and the embryonic axis that started as spots or dashes and rapidly invaded large areas of tissue so that quantification was impossible.

The combination of scores from 1. and 2. gave an average of 6 spots per embryo with a range of 0-64 spots.

Control embryos (30) derived from inoculations with the EHA101 carrying only pEHA 101 and no vector plasmid strain produced no blue staining of any sort with X-gluc. No staining of EHA101 containing SCVsulugi was observed either.

Histochemical Staining 14 Days Post-Inoculation

The staining pattern in these embryos was slightly different to that seen at 4 days. The staining was usually in the form of small spots, or sometimes as small zones. The average number of spots/zones per embryo was 3, with a range of 0-25. The embryo with the maximum number of staining events, also had more of the less commonly observed blue 'zones' on the scutellar tissue.

Callus Development

After 4 weeks growth, callus derived from the inoculated embryos was very similar to control callus obtained from uninoculated embryos. Presence of the bacteria did not appear to have substantially reduced the embryogenic capacity of the callus derived from the inoculated embryos.

Histochemical Staining One Month Post-Inoculation

Of the remaining 55 immature embryo-derived calli that were stained in x-gluc 16 showed evidence of GUS expression in the form of darkly stained blue cells. In 6 of these calli, quite large dark blue regions of staining were observed, up to 1 mm in diameter, and appearing as highly delineated areas, see FIG. 4. Three of the blue regions showed three-dimensional structure in the form of cell protrusions from the callus surface (as in FIG. 5), and were assessed as being in embryogenic callus, with good potential for regeneration.

The recovery of three stable integration events with good regeneration potential from this experiment, suggests that this method has a high transformation efficiency.

Example 2

Transformation of Wheat Using Seed Inoculation Method—Transformation and Regeneration of Transgenic Plants As for example 1 except that 187 embryos were inoculated and isolated, and these were subjected to a selection step.

Selection of Transformed Callus

After 12 days cultivation on W3T, embryogenic calli were transferred to W3 media with 2 mg/l Asulam and 150 mg/l Timentin (W32AT). Calli were maintained on this media for a further 2 weeks and then each callus was divided into 2 mm pieces and re-plated onto W32AT.

After a further 2 weeks culture, all tissue was assessed for development of embryogenic callus: any callus showing signs of continued development after 4 weeks on selection was transferred to regeneration media (RMT-MS with 40 g/l maltose and 150 mg/l Timentin, pH5.8, solidified with 6 g/l agarose, Sigma type I). Shoots were regenerated within 4 weeks on this media and then transferred to MS30 with 150 mg/l Timentin for shoot elongation and rooting.

Results

Transformation was determined by one or more of the following methods:

a) GUS histochemical staining (Jefferson, 1987) on at least roots and leaves b) PCR analysis for the sul gene. PCR analysis was performed on genomic DNA extracted from 1-2 $cm^2$ fresh leaf material using miniprep method described by Stacey and Isaac (Methods in Molecular Biology, Vol. 28: Protocols for nucleic acid analysis by nonradioactive probes, 9-15, Humana Press Inc., Totawa, N.J. (1994)). PCR reaction were performed using primers designed to amplify a 380 bp Sul fragment (5' TTGT-GCGGTTCTTCGAGGCG 3' and 5' TGCGCTTCGCA-GATCTCCAG 3'. Reactions conditions were as followed "hot start" (94° C., 3 min) followed by 30 cycles of denaturation (95° C., 30 s), annealing (60° C., 30 s), extension (73° C., 2 min) followed by 1 cycle at 73° C. (5 min) and then held at 24° C., c) Southern Analysis.

Southern analysis was performed on DNA from a full scale (9 ml) extraction from lyophilized ground tissue (Stacey and Isaac, 1994). DNA samples were adjusted to 0.2 mg/ml and digested with restriction enzymes HindIII, EcoRI and KpnI. Restriction enzyme digestion, gel electrophoresis and vacuum blotting were carried out as described by Stacey and Isaac (1994). Digoxygenin-labelled Sul and GUS probes were produced by PCR according to the method of McCreery and Helentjaris (Methods in Molecular Biology, Vol. 28: Protocols for nucleic acid analysis by nonradioactive probes, 67-71, Humana Press Inc., Totawa, N.J. (1994)). Hybridization of the probes to the Southern blot and detection by chemiluminescence was performed according to the method of McCreery and Helentjaris (Methods in Molecular Biology, Vol. 28; Protocols for nucleic acid analysis by nonradioactive probes, 107-112, Humana Press Inc., Totawa, N.J. (1994)).

d) Segregation Analysis of the T1 Generation.

Analysis was performed by histochemical staining on germinated seedlings.

2 Plants representing 2 separate transformation events (1.1% efficiency) were regenerated, leaf and root samples of which showed strong GUS expression by histochemical staining. Stable transformation was confirmed by Southern analysis and assessment of gene segregation in the progeny.

In a separate experiment, 116 embryos have been inoculated and 4 separate GUS posisite transgenic lines regenerated.

The efficiencies obtained (1.1 and 3.4%) are comparable with those obtained with other combinations of vectors and bacterial strains (see example 5).

Example 3

Transformation of Maize by Seed Inoculation Method—Transient Expression, Production of Transgenic Callus and Regeneration of Transformed Plants

Construct Preparation

As for example 1.

Preparation of *Agrobacterium* for Experiments

*Agrobacterium* is incubated on solidified YEP media with appropriate antibiotics at 27° C. for 2 days. Bacteria is then collected and re-suspended in TSIM1 (MS media with 100 mg/l myo-inositol, 10 g/l glucose, 50 mg/l MES buffer pH5.5) containing 100-400 μM acetosyringone to a density of 2.0-2.4 at 650 nm.

Preparation of Plant Material

Sections of maize plants, variety A188, (glasshouse grown at 20-35° C., 16 hr day) are excised to include at least the stem node below and the stem node above an ear/cob, 6-14 days post anthesis, and with at least one leaf retained. The husk leaves of the cob are carefully pulled down to expose the immature seed, and all silks removed.

With a sharp implement, every second longitudinal row of immature seed is carefully removed and discarded, and the whole lightly sprayed with 70% ethanol.

Inoculation of Maize Ears

Inoculation as for example 1. Plant sections are subsequently placed in water and the husk leaves replaced over the cob to prevent seed dehydration—covering with a plastic bag may also be advised. Material is then placed in a lit incubator at 23-25° C. for 2-5 days.

Embryo Isolation and Culture

As described by Ishida et al, 1997. Embryos are removed 2 days post isolation for transient expression analysis, and the remainder subjected to a selection step in order to regenerate stably transformed maize plants.

Example 4

Transient Expression in Immature Wheat Embryos Following Seed Inoculation, in the Absence of the Inducer Acetosyringone

Construct Preparation

As for example 1.

Preparation of *Agrobacterium* for Experiments

As for example 1 with the exception that acetosyringone was excluded from the inoculation media, and a lower concentration of *Agrobacterium* was used (OD 2.1 at 650 nm).

Preparation of Plant Material

As for example 1.

Inoculation of Tillers

As for example 1.

Embryo Isolation and Culture

Isolation as for example 1. After 2 days on W3T, 77 embryos were assessed for GUS expression by histochemical analysis in X-gluc.

Results

Blue spots/dashes were visible on the upper and lower surfaces of the scutellum, and in many cases, spots appeared to be incorporated into the scutellum structure, that is, were between the upper and lower epidermis. A few embryos had no evidence of GUS expression at all. The mean number of spots per embryo was 25.4 with a range of 0-252.

Other Embodiments

It is to be understood that, while the invention has been described in conjunction with the detailed description thereof, the foregoing description is intended to illustrate and not to limit the scope of the invention. Other aspects, advantages and modifications are within the scope of the claims as set forth below.

Example 5

Stable Transformation of Wheat by Seed Inoculation Method

Preparation of Construct and Introduction to *Agrobacterium* Strain LBA4404

The XhoI, XbaI fragment containing the $Sul^R$ from pWP258 (See example 1) is introduced in XhoI, XbaI cut pSB11 (Komari et al., Plant J. (1996) 10:165-174) creating pFFFII. The HindIII pUbi-GUSint fragment from pBBB (See example 1) is cloned into pFFFII cut by HindIII, to form pSB11 Sulugi (see FIG. 6).

This construct was introduced into *Agrobacterium tumefaciens* strain LBA4404(pSB1) (Komari et al., 1996), by electroporation and subsequent selection on 50 mg/l Spectinomycin to form super binary vector pSB111 Sulugi by recombination.

Preparation of Bacteria for Inoculation.

*Agrobacterium* was grown and resuspended using the method from example 1 but with varying amounts of acetosyringone (0-400 μM) in the inoculation media.

Inoculation of Seed

Method for example 1, experiments containing 50-300 embryos, see Table 1.

Tissue Culture of Isolated Embryos

See example 2.

Results

See Table 1.

Data in Table 1 represents successful experiments—the few experiments that did not yield plants were excluded. Transformation was determined by one or more of the following methods:

a) GUS histochemical staining (Jefferson, 1987) on at least roots and leaves b) PCR analysis for the sul gene.

c) Southern analysis.

d) Segregation analysis of the T1 generation.

Transformation Efficiencies

Transformation efficiencies of successful experiments ranged from 0.5-5.8%, with a mean of 1.5%. Transformed plants were regenerated from experiments initiated both with and without the inducer acetosyringone in the inoculation media. Transmission of the GUS gene into the T1 generation was confirmed for several lines, see Table 1.

The transformation efficiencies obtained were comparable or higher than any wheat transformation efficiencies published (Vasil et al., Bio/Technology (1992), 10: 667-674, Weeks et al., Plant Physiol. (1993), 102: 1077-1084, Nehra et al., Plant J. (1994), 5: 285-297, Becker et al., Plant J. (1994), 5: 299-307, Zhou et al., Plant Cell Rep. (1995), 15: 159-163, Cheng et al., (1997))

Integration Patterns

Gene integration patterns of transformed lines ranged from single insertions with Mendelian patterns of inheritance to multiple copy number lines with up to seven copies of the T-DNA.

Example 6

Transformation of Maize by Seed Inoculation Method—Transient Expression and Regeneration of Transformed Plants Construct Preparation As for example 1.

Or LBA 4404 (pSB131) described by Ishida et al., 1997.

Preparation of *Agrobacterium* for Experiments

*Agrobacterium* was incubated on solidified YEP media with appropriate antibiotics at 27° C. for 2 days. Bacteria was then collected and re-suspended in TSIM1 (MS media with 100 mg/l myo-inositol, 10 g/l glucose, 50 mg/l MES buffer pH5.5) containing 100-400 μM acetosyringone with 0-0.5% Pluronic acid F68 to a density of 2.0-2.4 at 650 nm.

Preparation of Plant Material

Sections of maize (*Zea mays* L.) plants, variety A188 or Hi II, (glasshouse grown at 20-35° C., 16 hr day) were excised to include at least the stem node below and the stem node above a cob, 6-14 days post anthesis, and with at least one leaf retained. The husk leaves of the cob were carefully pulled down to expose the immature seed, and all silks removed. The cob was lightly sprayed with 70% ethanol for sterilization.

Inoculation of Maize Ears

Inoculation as for example 1. Plant sections were subsequently placed in water and the husk leaves replaced over the cob covered and with cling film to prevent seed dehydration. Material was then placed in a lit incubator at 22-25° C. for 2-5 days.

Embryo Isolation and Culture

After co-cultivation the cob was sterilized 20 minutes in a 20% Domestos solution. The embryos were then aseptically isolated, rinsed twice in LSinf (Ishida et al, 1997) supplemented with 250 mg/l Cefotaxime and transferred to callus induction medium LSD (Ishida et al, 1997) for 2-10 days in the dark at 25° C.

Embryos were removed 2 days post isolation for transient expression analysis, and the remainder subjected to a selection step in order to regenerate stably transformed maize plants as described by Ishida et al, 1997.

Results

As shown in table 2, inoculation of immature embryos within the seed for maize led to transfer of T-DNA and expression of GUS gene with either strain used and for both varieties. Although only 3-10% of the immature embryos expressed GUS after co-cultivation, phosphinothricin resistant plants have been regenerated and expressed the GUS gene. The transformation frequencies could be considered as relatively high considering that the numbers of embryos put through selection for stable transformation was low. It also indicates that even if the T-DNA transfer is lower than a traditional full in vitro system (Ishida et al, 1997), the inoculation of the embryo in its natural seed environment targets cells that have a better potential for regeneration.

These results also show that this method is applicable to other monocot species and is not variety dependent regarding to the transformation step.

Example 7

Production of Transgenic *Brassica napes* Plants by Inoculation of *Agrobacterium* into the Base of Cotyledonary Petioles Construct Preparation P35S-nptII-tNOS Hind III fragment isolated from pCaMVNEO (Fromm et al., Nature (1996), 319: 791-793) was inserted into pSCV1 (Firek et al, Plant Mol. Biol. (1993) 22:129-142) to give pSCV1.2. The p35S-gus-intron-polyA-CaMVHind III fragment (Vancanneyt et al., M.G.G. (1990), 220: 245-250) was inserted in the Sma I site of pSCV1.2, resulting in pSCV1.2GI (FIG. 7)

This construct was introduced into *Agrobacterium tumefaciens* strain C58pMP90 (Koncz and Schell, 1986).

Seedling Preparation

Seeds of *Brassica napus* RV31, a spring variety, were surface sterilized using 15% Domestos for 20 minutes, followed by extensive washing with sterile water, to remove fungal and bacterial pathogens: Seeds (110) were then placed on germination media (MS media with 20 g/l sucrose) in Beatson jars (10 seed per jar) and placed at 25° C. with a 16 hr photoperiod for 3 days. Seedlings thus germinated are at the stage where the cotyledons and associated petioles have emerged but are not fully expanded.

Preparation of *Agrobacterium*

C58pMP90 SCV1.2GI was inoculated into 10 ml of mg/l media with appropriate antibiotic selection and grown at 28° C. on a rotary shaker for approximately 24 hours. The overnight culture was then centrifuged at 2000 rpm for 20 minutes and the supernatant discarded. Pelleted bacteria were re-suspended in MS30 liquid (MS media containing 30 g/l sucrose) to an $OD_{650\ nm}$ of approximately 2.0 (2.175).

Inoculation of *Agrobacterium*

The bacterial suspension (0.5-1.0 μl) was injected into the area at the base of each cotyledonary petiole using a 10 μl Hamilton syringe. Seedlings were then transferred to 20° C. for 2 days.

Callus Induction and Plant Regeneration

Cotyledons were excised from the seedling and cultured essentially as per the method of Moloney et al., Plant Cell Reports (1989) 8: 238-242. The surface of excised *Brassica napus* cotyledonary petioles cultured in this way undergo a brief period of callus development from the exposed vascular bundle tissue before shoot meristems form in this callus, within 8 days of culture (Ono et al., Plant Cell Reports (1994) 14: 13-17).

Results

6 Transformed shoots were regenerated from the 200 excised cotyledonary petioles, as determined by x-gluc staining for the GUS gene and PCR analysis for the NptII gene, equivalent to a 3.0% transformation efficiency. 1 Further line was shown to contain the gene by PCR analysis but had no GUS activity by x-gluc staining. Analysis of the T1 generation of 5 of the GUS expressing transformed lines by x-gluc staining showed transmission of the GUS gene to the next generation with the following results:

| T1 Plants assessed for GUS activity | | | |
| --- | --- | --- | --- |
| Line | Positive | Negative | Ratio |
| 1 | 10 | 10 | 1:1 |
| 2 | 9 | 0 | 9:0 |

-continued

T1 Plants assessed for GUS activity

| Line | Positive | Negative | Ratio |
|------|----------|----------|-------|
| 3 | 21 | 0 | 21:0 |
| 4 | 19 | 0 | 19:0 |
| 5 | 14 | 1 | 14:1 |

Discussion

Inoculation of *Agrobacterium* into the base of cotyledonary petioles while they are still attached to the seedling represents a marked departure from the published transformation system where the petioles are excised first and then the *Agrobacterium* applied. Although physically difficult to perform, this method proved to be remarkably efficient with little practice. With several years experience, using the standard published method and the same *Brassica napus* variety, a routine 5-10% transformation efficiency can be obtained. To achieve 3.0% at the second attempt (an initial experiment achieved 1 transformed shoot from 80 explants—1.25%) using this new method is surprising. This further demonstrates the applicability of this method of gene delivery to any species where a tissue culture system with a callus phase exists—monocotyledon or dicotyledon.

Example 8

Transformation of Soybean by Seed Inoculation Method—Transient Expression

Construct Preparation

*Agrobacterium tumefaciens* strain LBA 4404 was transformed with the super-binary vector pVec 035 containing the GUS intron gene driven by the CaMV 35S promoter (Supplied by B. Pelissier, Aventis Crop Science, Lyon, Fr).

Preparation of *Agrobacterium* for Experiments

*Agrobacterium* was incubated on solidified YEP media with appropriate antibiotics at 27° C. for 2 days. Bacteria was then collected and re-suspended in TSIM1 (MS media with 100 mg/l myo-inositol, 10 g/l glucose, 50 mg/l MES buffer pH5.5) containing 0-400 µM acetosyringone to a density of 0.5-2.0 at 650 nm.

Preparation of Plant Material

Soybean plants *Glycine max* cv Jack were grown in glasshouse at a temperature of 23-25° C., with supplemented light to give a 14 hour day.

Inoculation of Soybean Seeds

Immature seeds were inoculated when the embryos were 3-7 mm in size. The injection of 0.5-1 µl of *Agrobacterium* suspension was performed as described in example 1 by delivering the suspension between the two cotyledons, through the pod and longitudinally to the embryo. The plants were then incubated at 23-25° C. for 2-5 days.

Embryo Isolation and Culture

After co-cultivation the immature seeds were removed and sterilized 20 minutes in a 20% Domestos solution. The embryos were then aseptically isolated transferred to callus induction medium MSI (MS medium and B5 vitamins with 60 g/l sucrose and 40 mg/l 2,4-D, solidified with 3 g/l Phytagel, adjusted to pH 7) supplemented with 350 mg/l Cefotaxime in light conditions at 27° C. After 2-10 days the embryos were used for histochemical GUS staining to assess T-DNA transfer efficiency.

Results

As shown in table 3, inoculation of soybean immature embryos within the seed and pod led to transfer of T-DNA and expression of GUS. GUS positives spots or areas were widely spread over the immature embryos and not necessarily associated with the wounding sites (FIG. 8). Unlike the SAAT transformation of soybean cotyledon method (Santarèm et al., Plant Cell Report (1998), 17: 752-759) this technique provides an easier transformation protocol and a higher regeneration potential as the target cells are not wounded.

Example 9

Transformation of Sunflower by Seed Inoculation Method—Transient Expression

Construct Preparation

C58C1 (pGV2260) (Simpson et al., Plant Mol. Biol. (1986), 6: 403-416) (pBin 19) (Bevan, Nuc. Acids Res. (1984), 12: 8711-8121)

C58pMP90 (pSCV1.2GI) (See example 7)

Preparation of *Agrobacterium* for Experiments

*Agrobacterium* was incubated on solidified YEP media with appropriate antibiotics at 27° C. for 2 days. Bacteria was then collected and re-suspended in TSIM1 (MS media with 100 mg/l myo-inositol, 10 g/l glucose, 50 mg/l MES buffer pH5.5) containing 0-400 µM acetosyringone to a density of 2.0-2.4 at 650 nm.

Preparation of Plant Material

Sunflower plants *Helianthus annuus* cv HA300B were grown in glasshouse 15-30° C. with supplemented light to give a 14 hour day.

Inoculation of Sunflower Seeds

Immature seeds were inoculated 10 to 25 days post-anthesis. The injection of 1 µl of *Agrobacterium* suspension was performed as described in example 1 through the micropyle to be delivered between the two cotyledons. The capitulum was then incubated at 22-25° C. for 2-5 days.

Embryo Isolation and Culture

After co-cultivation the immature seeds were removed and sterilized 20 minutes in a 20% Domestos solution. The embryos were then aseptically isolated, transferred to callus induction medium (MS with 30 g/l sucrose, solidified Agar-agar 10 g/l, pH 5.7 and supplemented with 0.5 mg/l NAA, 0.5 g/l BAP and 500 mg/l Cefotaxime) and cultured at 21-24° C., 16 hr day, 30 $\mu Em^{-2}s^{-1}$ PAR. After 2-10 days the embryos were used for histochemical GUS staining to assess T-DNA transfer efficiency.

Results

As shown in table 4, inoculation of sunflower immature embryos within the seed led to transfer of T-DNA and expression of GUS gene with either strain used (5.9%-65.4%). GUS positives spots were mainly located on the cotyledons, but transformation events have been also located on the hypocotyl. Only two experiments have been laid down to assess the potential of the seed inoculation method to transform sunflower immature embryos. Surprisingly it has proven to be very efficient even if a critical parameter seems to be the development of the immature embryo.

TABLE 1

Transformation efficiencies for wheat immature embryos using seed inoculation method

| Experiment | Treatment | Number Embryos Isolated (X) | Number of embryos regenerating transgenic plants | Number of transgenic events (Y) | Efficiency (Y/X%) | Transmission to progeny |
|---|---|---|---|---|---|---|
| 1 | +AS | 86 | 1 | 5 | 5.8 | Yes |
| 2 | +AS | 144 | 1 | 1 | 0.7 | Yes |
| 3 | +AS | 159 | 1 | 1 | 0.6 | Yes |
| 4a | −AS | 146 | 1 | 1 | 0.7 | Yes |
| 4b | +AS | 150 | 1 | 2 | 1.3 | Yes |
| 5 | −AS | 214 | 1 | 1 | 0.5 | Yes |
| 7 | +AS | 283 | 5 | ND | $\geq 1.8$ | ND |
| 9 | +AS | 135 | 2 | ND | $\geq 1.5$ | ND |
| 11 | +AS | 155 | 2 | ND | $\geq 1.3$ | ND |
| 14 | +AS | 154 | 1 | ND | $\geq 0.6$ | ND |
| 15 | +AS | 105 | 2 | ND | $\geq 1.9$ | ND |
| | | | | | Mean $\geq 1.5\%$ | |

TABLE 2

Efficiency of T-DNA delivery and transformation efficiency by seed inoculation of maize.

| | LBA 4404 (pSB131) | EHA101 (pSCVSulugi) |
|---|---|---|
| A188 | | |
| Transient GUS expression Embryos GUS positive/Embryos tested (%) | 36/1345 (2.7%) | 33/393 (8.4%) |
| Stable Transformation efficiency (Events regenerated/Embryos in selection) | 2/421 (0.5%) | |
| Hi II | | |
| Transient GUS expression Embryos GUS positive/Embryos tested (%) | 20/381 (9.2%) | 7/66 (10.6%) |
| Stable Transformation efficiency (Events regenerated/Embryos in selection) | 5/225 (2.2%) | |

TABLE 3

Efficiency of T-DNA delivery by seed inoculation method in soybean

| Experiments | 1 | 2 | 3 |
|---|---|---|---|
| Embryos inoculated | 27 | 40 | 42 |
| Agrobacterium OD | 0.5 | 1.0 | 0.5 |
| Acetosyringone (μM) | 400 | 400 | 200 |
| Days of Co-cultivation | 2 | 5 | 5 |
| Positive Cotyledons /Cotyledons Tested | 0/24 | 2/30 | 3/38 |
| Callus induction | — | 7 | 6 |
| Positive Cotyledons/Cotyledons Tested | — | 2/35 | 0/40 |
| % of cotyledons with GUS positive spots | 0% | 6.2% | 3.8% |

TABLE 4

Efficiency of T-DNA transfer to sunflower immature embryos by seed inoculation.

| | C58pGV2260 pBin 19 | C58pMP90 pSCV1.2GI | |
|---|---|---|---|
| Days after anthesis | 21 | 16 | 13 |
| Embryos inoculated | 107 | 17 | 70 |
| Callus induction | 7 | 6    14 | 6    14 |
| Positive Embryos/ Embryos tested | 34/52 | 0/11    1/6 | 0/31    0/38 |
| % of explants with GUS positive spots | 65.4% | 5.9% | 0.0% |

What is claimed is:

1. A method of generating a transgenic dicotyledon plant, comprising:
    inoculating and co-cultivating a target tissue, from a target dicotyledon plant, with *Agrobacterium*, at a time when said target tissue is in its natural plant environment, wherein said inoculation is performed by injection of an *Agrobacterium* suspension into the target tissue with a syringe;
    removing said target tissue from its natural environment; and
    generating a transgenic plant via dedifferentiation and regeneration of said target tissue, wherein at least some of the dedifferentiation of the target tissue is carried out in vitro, wherein the target area for inoculation is at the base of the cotyledonary petiole or between the two cotyledons, while the cotyledons are still attached to an embryo in a seed or are attached to a seedling.

2. The method of claim 1, wherein the transgenic plant is a fertile plant.

3. The method of claim 1, wherein wounding of the target cells in the target tissue is kept to a minimum or totally excluded.

4. The method of claim 1, wherein no *Agrobacterium* vir inducing agent is added around the time of the *Agrobacterium* inoculation.

5. The method of claim 1, wherein no *Agrobacterium* vir inducing agent is added around the time of the Agrobacterium co-cultivation.

6. The method of claim 1, wherein the target plant is selected from the group consisting of rape, pepper, pea, soybean, sunflower, sugar beet, and cucurbit.

* * * * *